US011395767B2

(12) United States Patent
Van Den Berg

(10) Patent No.: US 11,395,767 B2
(45) Date of Patent: *Jul. 26, 2022

(54) COVERING DEVICE

(71) Applicant: Jan Dirk Johannes Van Den Berg, Welkom (ZA)

(72) Inventor: Jan Dirk Johannes Van Den Berg, Welkom (ZA)

(73) Assignee: Jan Dirk Johannes Van Den Berg, Welkom (ZA)

( * ) Notice: Subject to any disclaimer, the term of this patent is extended or adjusted under 35 U.S.C. 154(b) by 0 days.

This patent is subject to a terminal disclaimer.

(21) Appl. No.: 16/987,962

(22) Filed: Aug. 7, 2020

(65) Prior Publication Data

US 2020/0360188 A1  Nov. 19, 2020

Related U.S. Application Data

(63) Continuation-in-part of application No. 16/326,148, filed as application No. PCT/ZA2017/050042 on Aug. 16, 2017, now Pat. No. 10,788,155.

(30) Foreign Application Priority Data

Aug. 16, 2016  (ZA) ................................. 2016/05651
Oct. 26, 2016  (ZA) ................................. 2016/07365
(Continued)

(51) Int. Cl.
*F16L 55/17* (2006.01)
*A61F 13/00* (2006.01)

(52) U.S. Cl.
CPC .............. *A61F 13/00* (2013.01); *F16L 55/17* (2013.01); *A61F 2013/0028* (2013.01); *A61F 2013/00165* (2013.01); *A61F 2013/00272* (2013.01)

(58) Field of Classification Search
CPC ..... F16L 55/1686; F16L 55/17; F16L 55/172; F16L 3/2334
(Continued)

(56) References Cited

U.S. PATENT DOCUMENTS 4,585,091 A ‡ 4/1986 Budd ....................... F01N 13/18
                                                                    137/15.08
5,002,093 A ‡ 3/1991 Connolly, Jr. .......... F16L 55/17
                                                                    138/97
(Continued)

FOREIGN PATENT DOCUMENTS

CN         204554226 U      8/2015
FR         3006014 A1 ‡ 11/2014 .......... F16L 55/1686
(Continued)

OTHER PUBLICATIONS

Wagner S. (Authorized Officer), International Search Report dated Jan. 17, 2018, PCT Application No. PCT/ZA2017/050042, 6 pages.

*Primary Examiner* — Patrick F Brinson
(74) *Attorney, Agent, or Firm* — MH2 Technology Law Group LLP

(57) ABSTRACT

A covering device includes an elongate wrapping member configured to be wrapped around and overlay an opening in an object in a wrapped condition, a substantially shell-shaped cover member for covering the wrapping member substantially in the wrapped condition, and a retaining arrangement for retaining the cover member and with it, the wrapping member in position relative the object in a covering condition.

19 Claims, 10 Drawing Sheets

(30) Foreign Application Priority Data

Aug. 10, 2019 (ZA) .................................. 2019/02916
Dec. 4, 2019 (ZA) .................................. 2019/08039

(58) Field of Classification Search
USPC .................................................... 138/99, 97
See application file for complete search history.

(56) References Cited

U.S. PATENT DOCUMENTS

| | | | |
|---|---|---|---|
| 7,370,676 B2 ‡ | 5/2008 | d'Auria | F16L 55/175 138/132 |
| 7,900,655 B2 ‡ | 3/2011 | Morton | F16L 55/172 138/99 |
| 7,938,146 B2 ‡ | 5/2011 | Brooks | F16L 55/1683 138/97 |
| 8,141,592 B2 ‡ | 3/2012 | Rice | F16L 55/175 138/97 |
| 8,522,827 B2 ‡ | 9/2013 | Lazzara | B29C 63/10 138/172 |
| 9,784,401 B1 * | 10/2017 | Edwards | F16L 55/1715 |
| 10,612,713 B2 ‡ | 4/2020 | Walker | F16L 55/1686 |
| 2010/0012215 A1 * | 1/2010 | Morton | F16L 55/172 138/99 |
| 2015/0204475 A1 * | 7/2015 | Brooks | F16L 55/1683 138/99 |

FOREIGN PATENT DOCUMENTS

| | | |
|---|---|---|
| FR | 3006014 A1 | 11/2014 |
| GB | 2140529 A | 11/1984 |
| GB | 2485249 A | 5/2012 |
| JP | H0970884 A | 3/1997 |
| RU | 2156397 C1 | 9/2000 |

\* cited by examiner
‡ imported from a related application

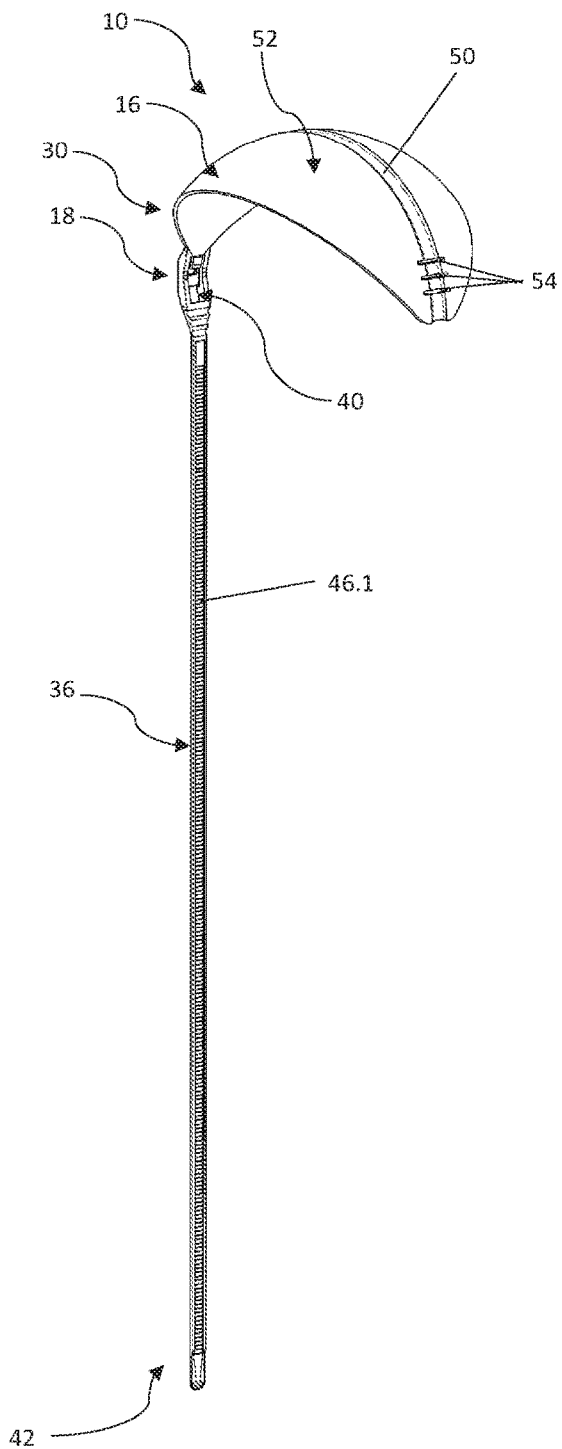
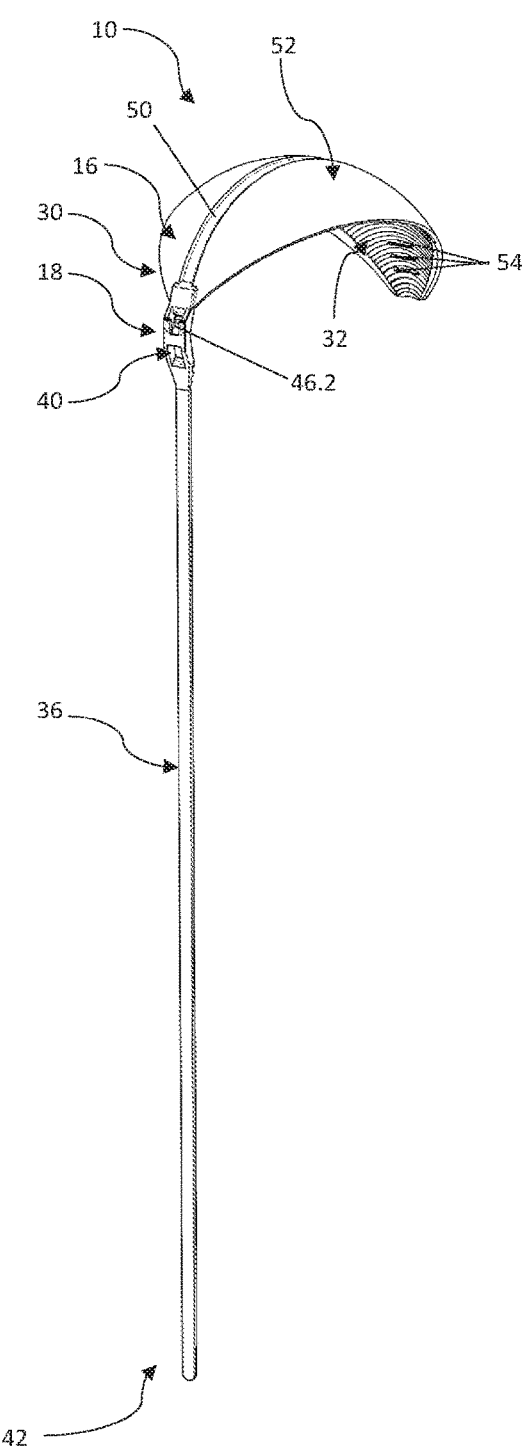

COVERING DEVICE

CROSS-REFERENCE TO RELATED APPLICATIONS

This application is a continuation-in-part of U.S. patent application having Ser. No. 16/326,148, which was filed on Feb. 15, 2019 and is a national-stage entry of PCT Patent Application No. PCT/ZA2017/050042, which was filed on Aug. 16, 2017 and claims priority to South Africa Patent Application No. 2016/07365 filed on Oct. 26, 2016, and South Africa Patent Application No. 2016/05651, which was filed on Aug. 16, 2016. This application also claims priority to South Africa Patent Application No. 2019/02916, which was filed on Aug. 10, 2019, and South Africa Patent Application No 2019/08039, which was filed on Dec. 4, 2019. Each of the priority applications listed above is incorporated herein by reference in its entirety.

FIELD

This invention relates to a covering device for covering and sealing a leak in a pipe, for covering and protecting a wound in a body part and for covering and insulating electrical wiring.

SUMMARY

According to a first aspect of the invention there is provided a covering device for covering an opening in an object which includes an elongate wrapping member which is configured to be wrapped around and overlay an opening in an object in a wrapped condition, a substantially shell-shaped cover member for covering the wrapping member substantially in the wrapped condition, and a retaining arrangement for retaining the cover member and with it, the wrapping member in position relative the object in a covering condition.

A connecting arrangement may be provided for allowing interconnection, e.g., releasable, between the wrapping member and the cover member. The connecting arrangement may include a receiving formation, e.g., defined in the cover member, for receiving the wrapping member therein. The receiving formation may be sized, shaped and/or configured to receive and retain the wrapping member in a connected condition relative the cover member. The receiving formation may be sized, shaped and/or configured to allow relative displacement between the cover member and the wrapping member in the wrapped condition so as to facilitate substantial overlaying of the wrapping member by the cover member. In particular, the receiving formation may be in the form of a plurality of slots which may be defined in the cover member for receiving the wrapping member therethrough for allowing a plurality of loops to be formed allowing the wrapping member to substantially overlay and retain itself in the connected condition. The plurality of slots may be positioned substantially parallel each other. Further, the plurality of slots may follow a generally curved or straight path. The slots may be substantially straight at an intermediate portion thereof and substantially curved at opposing end regions thereof. Alternatively, the connecting arrangement may be in the form of a buckle-like assembly for allowing releasable interconnection between the wrapping member and the cover member.

The shell-shaped cover member may have a substantially arcuate or curved profile so as to correspond with the curvature of the object having an opening to be covered and/or the curvature of the wrapping member in the wrapped condition. The profile of the cover member may be curved in both longitudinal and transverse directions so as to produce the substantially shell shape. In particular, the cover member may have a substantially spheroidal shape, e.g., resembling a portion of a substantially spherical shell. The cover member may have a substantially oblate or prolate spheroidal shape. More particularly, the cover member may be in the shape of any one of a quarter spherical shell, half hemispherical shell, and a spheroidal cap or dome. It is to be appreciated that the substantially spherical shell shape is capable of conforming to objects of various, typically substantially rounded, shapes upon tightening of the cover member around the object. The cover member may be sized so as to allow it to overlay the wrapping member in the wrapped condition, e.g., having a width that allows a free end region of the cover member to overlay itself at least partially in the covering condition. The cover member may include a gripping formation for gripping the elongate wrapping member in the covering condition. The gripping formation may be in the form of a plurality of ridges or teeth which may extend inwardly the cover member to grip the wrapping member in the covering condition. The ridges or teeth may extend at an angle away from the cover member for allowing directional gripping of the wrapping member thereby permitting tightening of the cover member around the wrapping member whilst inhibiting loosening of the cover member in the covering condition. In addition, ridges or teeth may extend from an outer surface of the cover member, which teeth may be configured to engage complementally the inwardly extending ridges or teeth for assisting in retaining the cover member in the covering condition, typically when the cover member wraps around a substantially rounded object and overlays itself. The outwardly extending ridges or teeth may extend at an angle away from the cover member for permitting tightening of the cover member over itself whilst inhibiting loosening thereof from the covering condition. The cover member may be manufactured from any suitable flexible material or composite of materials for allowing tightening and flush overlaying thereof with the wrapping member into the covering condition. In particular, the cover member may be manufactured from any suitable flexible synthetics or plastics material which may include any one or more of the group including polypropylene, polycarbonate, polyethylene, silicone, nylon, rubber, vulcanised rubber, reinforced vulcanised rubber, butyl rubber and polyvinyl chloride. It is to be appreciated that the flexibility of the cover member may allow a user to cover a wrapping member at an angle relative a longitudinal axis of a rounded object around which the wrapping member may be wrapped whilst maintaining substantially uniform application of force or pressure of the cover member to and around the wrapping member and/or the object.

The retaining arrangement may be mounted on the cover member. The retaining arrangement may include an elongate member which may extend from the cover member, e.g., from an end region thereof opposite the connecting arrangement. The retaining arrangement may further include a receiving zone for receiving a free end region of the elongate member therein. The receiving zone may be in the form of an aperture or slot which may be sized, shaped and/or configured to receive the free end region of the elongate member therethrough. The retaining arrangement may further include a retaining formation for retaining the elongate member in position relative the receiving zone. The retaining formation may be in the form of a rack-and-ratchet assembly, e.g., including engaging tooth formations extending from the elongate member and a wall of the receiving zone, respectively. Alternatively, the retaining arrangement may be in the form of any suitable clamping assembly for clamping an overlaying free end region of the elongate member relative itself and/or the cover member in the pipe sealing condition. The elongate member may include a gripping formation, e.g., in the form of a plurality of ridges, for facilitating retention of the elongate member when wrapped around the cover member in a wrapped condition. The ridges of the gripping formation may be manufactured from any suitable synthetics or plastics material, e.g., being manufactured from rubber. A plurality of receiving zones may be defined at various positions in the cover member for accommodating various angular configurations of the cover member relative a wrapped object. The retaining arrangement may be manufactured from any suitable flexible synthetics, plastics or metallic material which may include any one or more of the group including polypropylene, polycarbonate, polyethylene, silicone, nylon, rubber, vulcanised rubber, butyl rubber and polyvinyl chloride. In an alternative form of the invention, the retaining arrangement may include a pair of rings mounted on the cover member for receiving and retaining a free overlaying end region of the cover member during wrapping thereof around an object. First and second rings of the pair may be sized, shaped and/or configured to receive the free end region of the cover member therethrough and allow a user to loop the cover member back over the second ring, back through the first ring and pull the free end region so as to allow the cover member to overlay itself and tighten into the covering condition.

A locating formation may be defined in the cover member, e.g., an outer surface thereof, for locating the elongate member relative the cover member when the elongate member overlays the cover member, e.g., during the covering condition. The locating formation may be in the form of an elongate recess which may extend substantially along a length of the cover member. The elongate recess may be sized and/or shaped to correspond to the size and/or shape of the elongate member so as to allow seating thereof in the elongate recess in the pipe sealing condition. Further, the elongate recess may include tooth formations which may be sized, shaped and/or configured to engage with the tooth formations extending from the elongate member for assisting in retaining the cover member in the covering condition. Alternatively, the locating formation may be in the form of a protrusion which may be sized, shaped and/or configured to engage or grip the elongate member in the covering condition.

A release mechanism may be provided for allowing the elongate member to be released from the retaining formation and displaced relative the receiving zone out of the covering condition.

A second retaining arrangement may be provided for assisting in retaining an overlaying free end region of the elongate member in abutment with an overlaid portion of the cover member in the covering condition. The second retaining arrangement may be in the form of a band-like member for receiving and retaining the overlaying end region of the elongate member in seated abutment with the cover member. E.g., the second retaining arrangement may be in the form of a plurality of band-like members, which may be attached to the cover member in a region of the elongate recess for retaining the overlaying end region of the elongate member in seated abutment with the cover member within the elongate recess. Guides may be provided to allow the second retaining arrangement to be mounted displaceably on the cover member. Alternatively, the second retaining arrangement may be in the form of a rack-and-ratchet assembly. The second retaining arrangement may include an aperture defined in the cover member for allowing the overlaying free end region of the elongate member to be tucked between layers of overlapping cover member or between the cover member and the wrapping member.

A free end region of the wrapping member may be sized, shaped and/or configured to assist a user with initiating wrapping of the wrapping member in use. In particular, the free end region of the pipe wrapping member may include a handle formation for facilitating gripping of the free end region and allowing a user to wrap a remainder of the wrapping member around an object having an opening to be covered. Alternatively, the free end region of the wrapping member may be wider in width than an intermediate region thereof for facilitating initial wrapping thereof around the object. An aperture may be defined in the free end region of the wrapping member for allowing fastening thereof to a fixed support member, such as a hook, so as to facilitate wrapping and tightening of the wrapping member into the wrapped condition. An opposite end region of the wrapping member may be sized, shaped and/or configured, e.g., having a hardened tip, to facilitate receipt thereof by the receiving formation. Alternatively, the opposite end region of the wrapping member may be narrower in width in order to facilitate receipt thereof by the receiving formation. The wrapping member may be manufactured from any suitable elastic material which may include any one or more of the group consisting of polyurethane, natural rubber, synthetic rubber and latex.

A tightening means may be provided for tightening the elongate member around the cover member and wrapping member. The tightening means may include an aperture defined in the elongate member, e.g., towards the free end region thereof, for receiving an end region of a lever therethrough to allow a user to tighten the elongate member and cover member in the covering condition.

The cover member, retaining arrangement and/or the wrapping member may be integrally formed, e.g., being manufactured from rubber, further e.g., being manufactured from butyl rubber. The cover member may be manufactured from a rubber having a higher sulphur content than the wrapping member for improving physical properties of the cover member, such as for example, elasticity, resilience, tensile strength, viscosity and hardness.

The covering device may be utilised to cover and seal a leak in a pipe. Alternatively, the covering device may be utilised to cover and protect a wound in a body part. Further alternatively, the covering device may be utilised to cover and close an opening in an insulative electrical cover. In particular, the covering device may be sized, shaped and/or configured to be wrapped around an outer, e.g., insulative, covering of electrical wiring so as to facilitate substantial sealing of any crack, slit or opening therein so as to inhibit the ingress of fluid such as water therein.

According to a second aspect of the invention, there is provided a covering device for covering and protecting a wound, which covering device includes a substantially shell-shaped cover member for covering the wound, and a retaining arrangement for retaining the cover member in a wound covering condition wherein the wound is covered and protected.

The shell-shaped cover member may have a substantially arcuate or curved profile for allowing a wound in a body part, such as a limb, appendage and/or digit, to be covered and protected in a wound covering condition. In particular, the cover member may be sized, shaped and/or configured to cover a wound located in a joint of a body and permit substantially unencumbered displacement of the body part in the wound covering condition. Further, the cover member may be sized and/or shaped to accommodate and overlay a dressing applied to a wound in a body part. The cover member may have a substantially spheroidal shape, e.g., resembling a portion of a substantially spherical shell. More particularly, the cover member may be in the shape of a quarter spherical or half hemispherical shell.

The cover member may be manufactured from an elastic and/or flexible material for allowing covering of varying contours of a body part and allowing the cover member to at least partially wrap around a body part and overlay itself in a wound covering condition. It is to be appreciated that the flexibility and elasticity of the cover member further allows a user to cover wounds in body parts at varying angles depending on the position of the wound on the body part whilst maintaining substantially uniform application of force or pressure of the cover member to and around the body part and/or a dressing or bandage. In particular, the cover member may be manufactured from any suitable flexible synthetics or plastics material or composite of materials which may include any one or more of the group including polypropylene, polycarbonate, polyethylene, silicone, nylon, rubber, vulcanised rubber, reinforced vulcanised rubber and polyvinyl chloride. Alternatively, the cover member may be manufactured from a soft flexible material so as to improve comfort and reduce the likelihood of damaging the wound further or of causing pain. The cover may include an inner insert which may be manufactured from a material which facilitates conforming of the cover member to the body part. In particular, the insert may be manufactured from memory foam or the like.

The cover member may include a gripping means for gripping skin surrounding a wound in a body part and assisting in retaining the cover member in the wound covering condition. Further, the gripping means may be in the form of a ridge or tooth formation, e.g., being located on an underside of the cover member, for allowing gripping of a wound dressing applied to a wound for assisting in retaining the cover member and the wound dressing in the wound covering condition. Alternatively, the gripping means may be in the form of an adhesive for allowing the cover member to adhere to skin surrounding a wound so as to seal the wound off and inhibit the ingress of fluid, dirt, bacteria, or any other harmful matter into the wound. In addition, the adhesive may be configured to adhere to a wound dressing or bandage applied to the wound.

The cover member may include an absorbing member for absorbing excess blood and/or fluid which may be expelled from the wound.

The retaining arrangement may be mounted on the cover member. The retaining arrangement may include an elongate member which may extend from an end region of the cover member. The retaining arrangement may further include a receiving zone for receiving a free end region of the elongate member therein. The receiving zone may be in the form of an aperture or slot which may be sized, shaped and/or configured to receive the free end region of the elongate member therethrough. The retaining arrangement may further include a retaining formation for retaining the elongate member in position relative the receiving zone. The retaining formation may be in the form of a rack-and-ratchet assembly, e.g., including engaging tooth formations extending from the elongate member and a wall of the receiving zone, respectively. Alternatively, the retaining arrangement may be in the form of any suitable clamping assembly for clamping an overlaying free end region of the elongate member relative itself and/or the cover member in the wound covering condition. A plurality of receiving zones may be defined at various positions in the cover member for accommodating various angular configurations of the cover member relative a body part. The retaining arrangement may be manufactured from any suitable flexible synthetics, plastics or metallic material which may include any one or more of the group including polypropylene, polycarbonate, polyethylene, silicone, nylon, rubber, vulcanised rubber and polyvinyl chloride.

A locating formation may be defined in the cover member, e.g., an outer surface thereof, for locating the elongate member relative the cover member when the elongate member overlays the cover member, e.g., during the pipe sealing condition. The locating formation may be in the form of an elongate recess which may extend substantially along a length of the cover member. The elongate recess may be sized and/or shaped to correspond to the size and/or shape of the elongate member so as to allow seating thereof in the elongate recess in the wound covering condition. Further, the elongate recess may include tooth formations which may be sized, shaped and/or configured to engage with the tooth formations extending from the elongate member for assisting in retaining the cover member in the wound covering condition.

A second retaining arrangement may be provided for assisting in retaining an overlaying free end region of the elongate member in abutment with an overlaid portion of the cover member in the wound covering condition. The second retaining arrangement may be in the form of a band-like member, e.g., a plurality of band-like members, which may be attached to the cover member in a region of the elongate recess for retaining the overlaying end region of the elongate member in seated abutment with the cover member within the elongate recess.

A release mechanism may be provided for allowing the elongate member to be released from the retaining formation and displaced relative the receiving zone out of the wound covering condition.

The cover member and retaining arrangement may be integrally formed, e.g., being manufactured from rubber. In this case, the retaining arrangement may include a pair of rings mounted on the cover member for receiving and retaining a free overlaying end region of the cover member during wrapping thereof around a leak in a pipe. First and second rings of the pair may be sized, shaped and/or configured to receive the free end region of the cover member therethrough and allow a user to loop the cover member back over the second ring, back through the first ring and pull the free end region so as to allow the cover member to overlay itself and tighten into the pipe sealing condition.

It is to be appreciated that the covering device may be sized, shaped and/or configured to be wrapped around an outer, e.g., insulative, covering of electrical wiring so as to facilitate substantial sealing of any crack, slit or opening therein so as to inhibit the ingress of fluid such as water therein.

It is to be appreciated that the covering device may be sized, shaped and/or configured to be wrapped around an exhaust pipe so as to facilitate substantial sealing of any crack, slit or opening therein so as to inhibit the flow of exhaust gases therefrom.

BRIEF DESCRIPTION OF THE DRAWINGS

FIGS. 5 and 6 are three-dimensional schematics showing different views of a further covering device in accordance with the invention.

DETAILED DESCRIPTION

Figure 1:
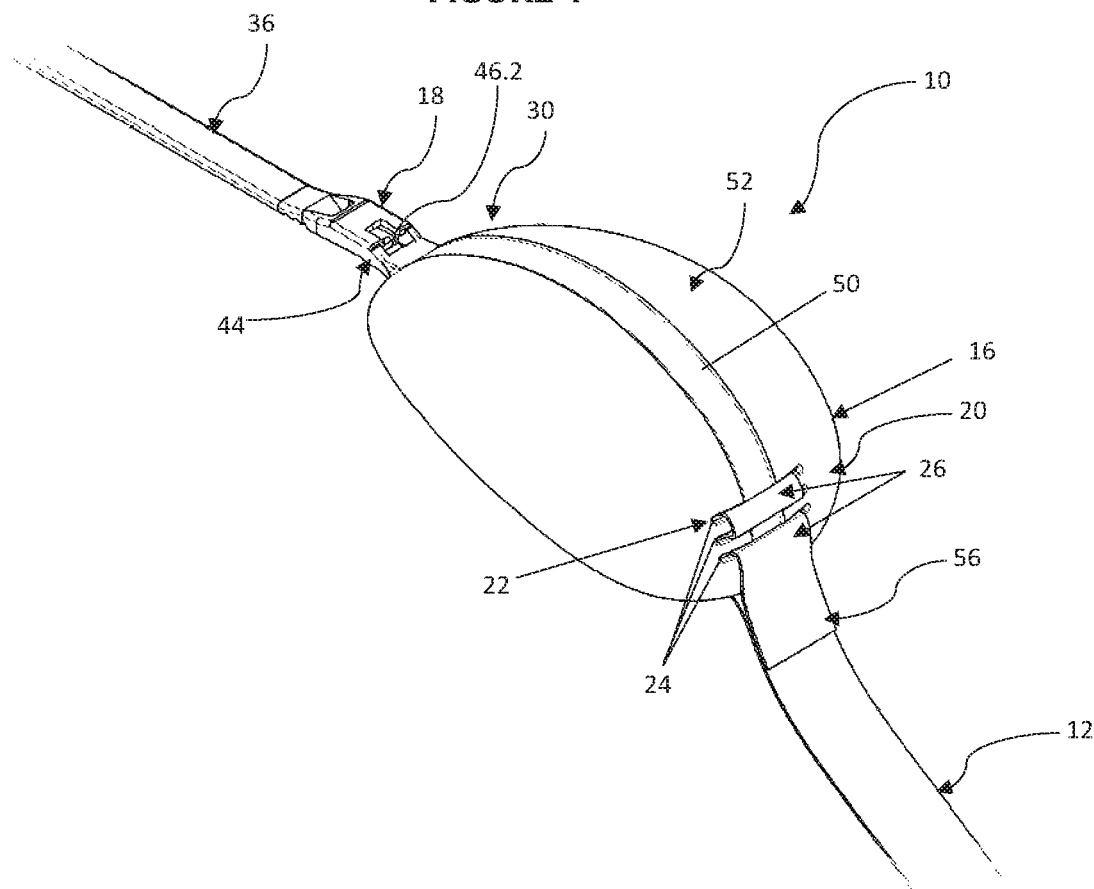
FIGS. 1 and 2 are three-dimensional schematics showing a top side region and an underside region, respectively, of a covering device in accordance with the invention.
Figure 2:
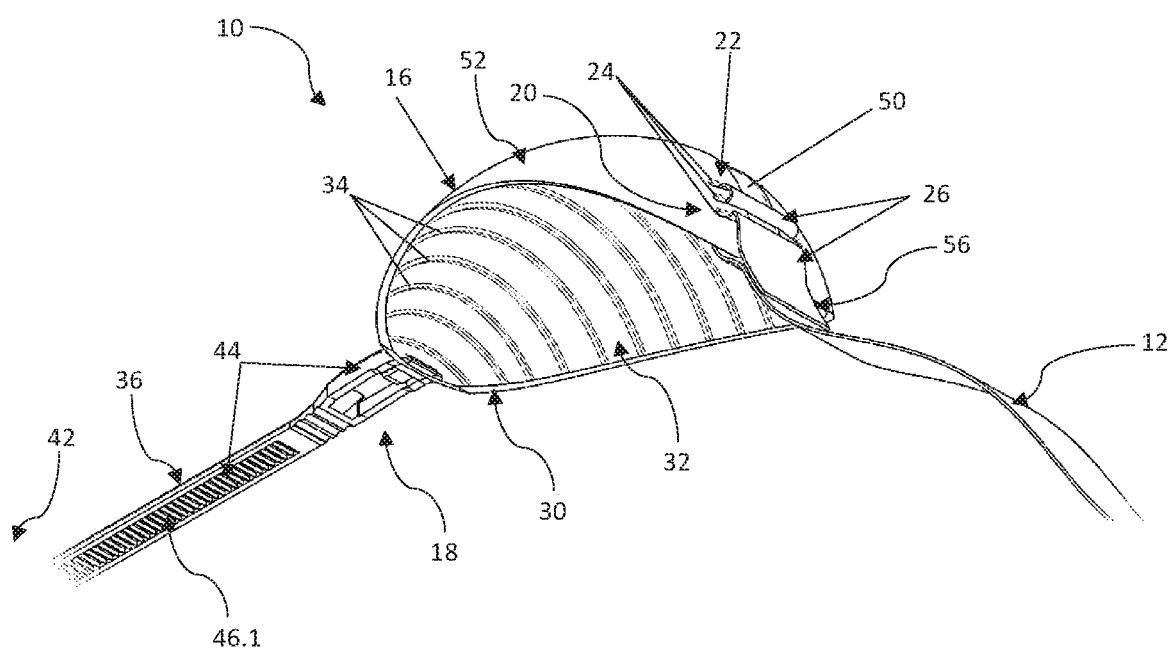
Figure 3:
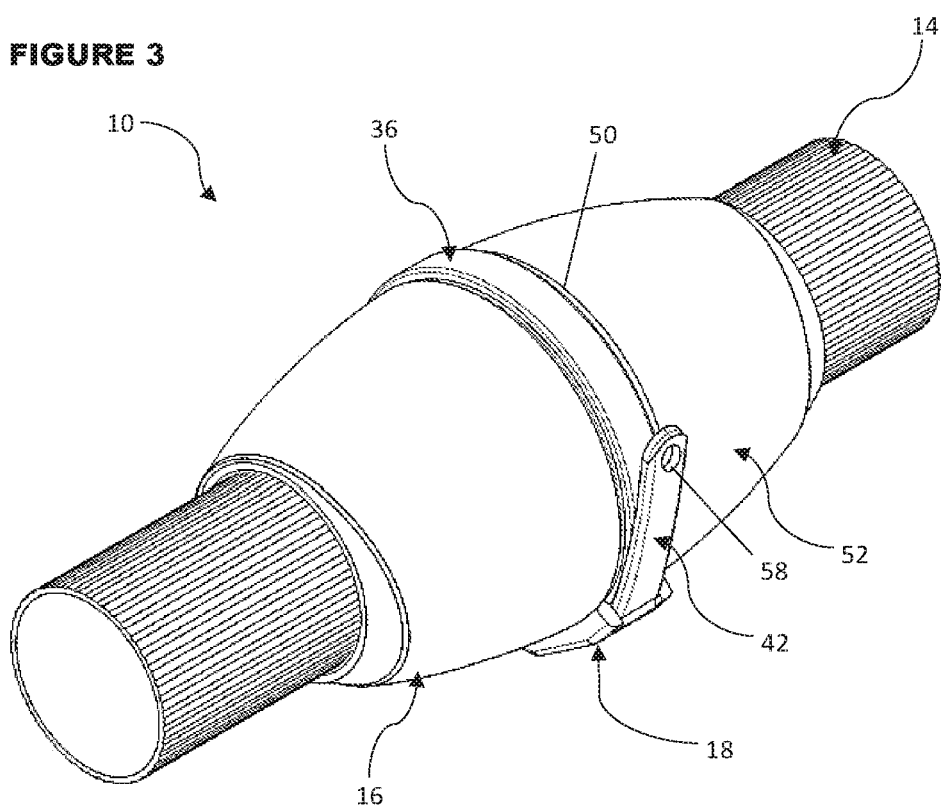
FIGS. 3 and 4 are three-dimensional schematics showing the covering device for covering and sealing a leak in a pipe in pipe sealing conditions in a straight and bent pipe, respectively.
Figure 4:
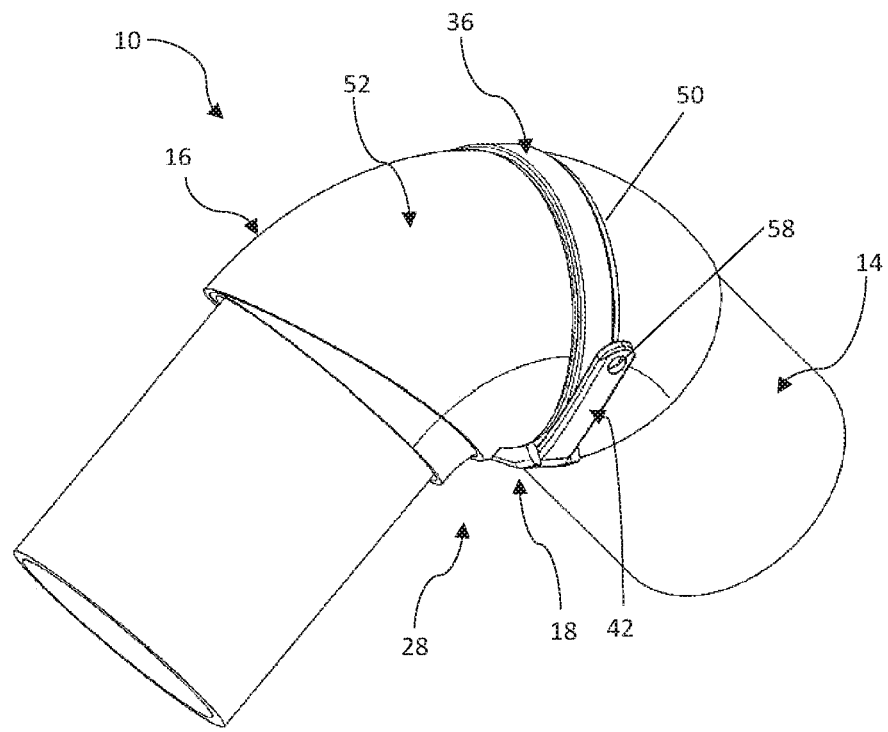

A covering device for covering and sealing a leak in a pipe and a covering device for covering and protecting a wound in accordance with the invention will now be described by way of the following non-limiting examples, with reference to the accompanying drawings herebelow.

Referring now to FIGS. 1 to 6, reference numeral 10 refers generally to a covering device for covering and sealing a leak in a pipe. The covering device 10 includes an elongate pipe wrapping member 12 which is configured to be wrapped around and overlay a leak (not shown) in a pipe 14 in a wrapped condition, a substantially shell-shaped cover member 16 for covering the pipe wrapping member 12 substantially in the wrapped condition and a retaining arrangement 18 for retaining the cover member 16 and with it, the pipe wrapping member 12 in position relative the pipe 14 in a pipe sealing condition.

A connecting arrangement 20 is provided for allowing interconnection, typically releasable, between the pipe wrapping member 12 and the cover member 16. The connecting arrangement 20 includes a receiving formation 22, typically defined in the cover member 16, for receiving the pipe wrapping member 12 therein. The receiving formation 22 is sized, shaped and configured to receive and retain the pipe wrapping member 12 in a connected condition relative the cover member 16. The receiving formation 22 is sized, shaped and configured to allow relative displacement between the cover member 16 and the pipe wrapping member 12 in the wrapped condition so as to facilitate substantial overlaying of the pipe wrapping member 12 by the cover member 16. In particular, the receiving formation 22 includes a plurality of slots 24 which are defined in the cover member for receiving the pipe wrapping member therethrough for allowing a plurality of loops 26 to be formed allowing the pipe wrapping member 12 to substantially overlay and retain itself in the connected condition. Although not shown, the connecting arrangement 20 can be in the form of a buckle-like assembly for allowing releasable interconnection between the pipe wrapping member 12 and the cover member 16.

The shell-shaped cover member 16 has a substantially curved profile so as to correspond with the curvature of the pipe to be sealed or repaired, or the curvature of the pipe wrapping member 12 in the wrapped condition. In particular, the cover member 16 has a substantially spheroidal shape, typically resembling a portion of a substantially spherical shell. More particularly, the cover member 16 is in the shape of a quarter spherical or half hemispherical shell, as most clearly shown in FIGS. 5a and 5b. The cover member can be in the form of a spheroidal cap or dome. It is to be appreciated that the substantially spherical shell shape is capable of sealing leaks in substantially straight pipes 14 whilst being capable of accommodating leaks located in a bend 28 of a pipe 14 and further, the shape of the cover member permits sealing of leaks formed in joints of different sized pipes. The cover member 16 is sized so as to allow it to overlay the pipe wrapping member 12 in the wrapped condition, typically having a width that allows an end region 30 of the cover member 16 to overlay itself at least partially in the pipe sealing condition. The cover member 16 includes a gripping formation 32 for gripping the elongate pipe wrapping member 12 in the pipe sealing condition. The gripping formation 32 is in the form of ridges or teeth 34 which extend inwardly the cover member 16 to grip the pipe wrapping member 12 in the pipe sealing condition. The ridges or teeth 34 extend at an angle away from the cover member 16 for allowing directional gripping of the pipe wrapping member 12 thereby permitting tightening of the cover member 16 around the pipe wrapping member 12 whilst inhibiting loosening of the cover member 16 out of the pipe sealing condition. In addition, ridges or teeth (not shown) can extend from an outer surface of the cover member 16, which ridges or teeth (not shown) is configured to engage complementally the inwardly extending ridges or teeth 34 for assisting in retaining the cover member 16 in the pipe sealing condition, typically when the cover member wraps around a pipe and overlays itself. The outwardly extending teeth (not shown) extend at an angle away from the cover member 16 for permitting tightening of the cover member 16 over itself whilst inhibiting loosening thereof from the pipe sealing condition. The cover member 16 is manufactured from any suitable flexible material or composite of materials, for allowing tightening and flush overlaying thereof with the pipe wrapping member 12 into the pipe sealing condition. In particular, the cover member 16 is manufactured from any suitable flexible synthetics or plastics material which includes any one or more of the group including polypropylene, polycarbonate, polyethylene, silicone, nylon, rubber, vulcanised rubber, reinforced vulcanised rubber, butyl rubber and polyvinyl chloride. Although not shown, it is to be appreciated that the flexibility of the cover member 16 may allow a user to cover a pipe wrapping member 12 at an angle relative a longitudinal axis of a pipe 14 around which the pipe wrapping member 12 is wrapped whilst maintaining substantially uniform application of force or pressure of the cover member to and around the pipe wrapping member and/or the pipe.

The retaining arrangement 18 is mounted on the cover member 16. The retaining arrangement 18 includes an elongate member 36 which extends from the cover member 16, typically from the end region 30 thereof opposite the connecting arrangement 20. The retaining arrangement 18 further includes a receiving zone in the form of an aperture or slot 40 for receiving a free end region 42 of the elongate member 36 therein, typically when the elongate member is wrapped around the cover member. The aperture or slot 40 is sized, shaped and configured to receive the free end region 42 of the elongate member 36 therethrough. The retaining arrangement 18 further includes a retaining formation in the form of a rack-and-ratchet assembly 44 for retaining the elongate member 36 in position relative the receiving zone 40. The rack-and-ratchet assembly 44 typically includes engaging tooth formations 46.1 and 46.2 extending from the elongate member 36 and a wall of the receiving zone 40, respectively. Although not shown, the retaining arrangement 18 is in the form of any suitable clamping assembly (not shown) for clamping an overlaying free end region 42 of the elongate member 36 relative itself or the cover member 16 in the pipe sealing condition. A plurality of receiving zones (not shown) is defined at various positions in the cover member 16 for accommodating various angular configurations of the cover member 16 relative a wrapped pipe (this is now shown). The retaining arrangement 18 is manufactured from any suitable flexible synthetics, plastics or metallic material which includes any one or more of the group including polypropylene, polycarbonate, polyethylene, silicone, nylon, rubber, vulcanised rubber and polyvinyl chloride.

A locating formation in the form of an elongate recess 50 is defined in the cover member 16, typically an outer surface 52 thereof, for locating the elongate member 36 relative the cover member 16 when the elongate member 36 overlays the cover member 16, typically during the pipe sealing condition. The elongate recess 50 extends substantially along a length of the cover member 16. The elongate recess 50 is sized and shaped to correspond to the size and shape of the elongate member 36 so as to allow receiving and seating thereof in the elongate recess 50 in the pipe sealing condition. Although not shown, the elongate recess 50 can include tooth formations (not shown) which are sized, shaped and configured to engage with the tooth formations 46.1 extending from the elongate member 36 for assisting in retaining the cover member 16 in the pipe sealing condition.

A release mechanism (not shown) is provided for allowing the elongate member 36 to be released from the retaining formation 44 and displaced relative the receiving zone 40 out of the pipe sealing condition.

A second retaining arrangement, in the form of a plurality of band-like members 54, is provided, as shown in FIGS. 5a and 5b, for assisting in retaining an overlaying free end region (not shown) of the elongate member 36 in seated abutment with an overlaid portion of the cover member 16 in the pipe sealing condition. The plurality of band-like members 54 are attached to the cover member 16 in the region of the elongate recess 50 for retaining the overlaying end region of the elongate member in seated abutment with the cover member 16 within the elongate recess 50. Guides (not shown) can be provided to allow the second retaining arrangement to be mounted displaceably on the cover member 16.

A free end region (not shown) of the pipe wrapping member 12 is sized, shaped and configured to assist a user with initiating wrapping of the pipe wrapping member 12 in use. In particular, the free end region of the pipe wrapping member 12 includes a handle formation (not shown) for facilitating gripping of the free end region (not shown) and allowing a user to wrap a remainder of the pipe wrapping member 12 around a pipe to be sealed. An aperture (not shown) is defined in the free end region (not shown) of the pipe wrapping member 12 for allowing fastening thereof to a fixed support member (not shown), such as a hook, so as to facilitate wrapping and tightening of the pipe wrapping member 12 into the pipe wrapping condition. An opposite end region 56 of the pipe wrapping member 12 is sized, shaped and configured, typically having a hardened tip (not shown), to facilitate receipt thereof by the receiving formation 22. The pipe wrapping member 12 is manufactured from any suitable elastic material which includes any one or more of the group consisting of polyurethane, natural rubber, synthetic rubber and latex.

A tightening means in the form of an aperture 58 is provided for tightening the elongate member 36 around the cover member 16 and pipe wrapping member 12. The includes aperture 58 is defined in the elongate member 36, typically towards the free end region 42 thereof, for receiving an end region of a lever (not shown) therethrough to allow a user to tighten the elongate member 36 and cover member 16 in the pipe sealing condition.

The cover member 16, retaining arrangement 18 and the pipe wrapping member 12 are integrally formed and manufactured from rubber, typically butyl rubber. The cover member 16 can be manufactured from a rubber having a higher sulphur content than the pipe wrapping member 12 for improving physical properties of the cover member 16, such as for example, elasticity, resilience, tensile strength, viscosity and hardness. Although not shown, in this case, the retaining arrangement 18 can include a pair of rings mounted on the cover member 16 for receiving and retaining a free overlaying end region of the cover member 16 during wrapping thereof around a leak in a pipe. First and second rings of the pair (not shown) are sized, shaped and configured to receive the free end region of the cover member 16 therethrough and allow a user to loop the cover member 16 back over the second ring, back through the first ring and pull the free end region so as to allow the cover member 16 to overlay itself and tighten into the pipe sealing condition.

Although the specific description above describes the covering member 10 for use in sealing a leak in a pipe, it is to be appreciated that the covering device 10 can be utilised to cover and protect a wound in a body part and to cover and close an opening in an insulative electrical cover.

Figure 7:
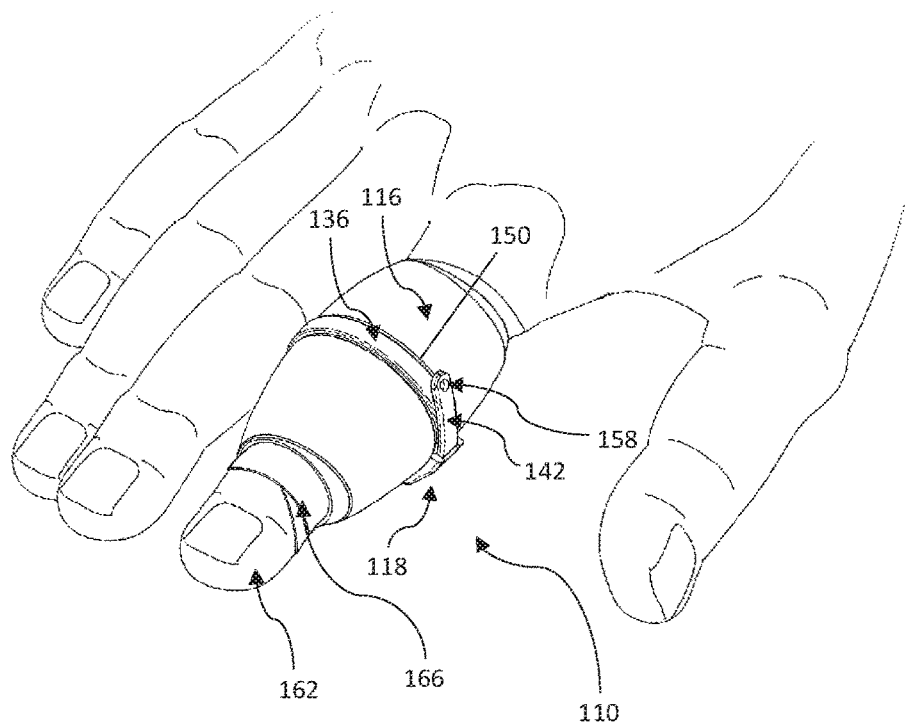
FIGS. 7 and 8 are three-dimensional schematics showing a covering device being utilised to cover and protect a wound in wound covering conditions for wounds in different joints of a finger, respectively.
Figure 8:
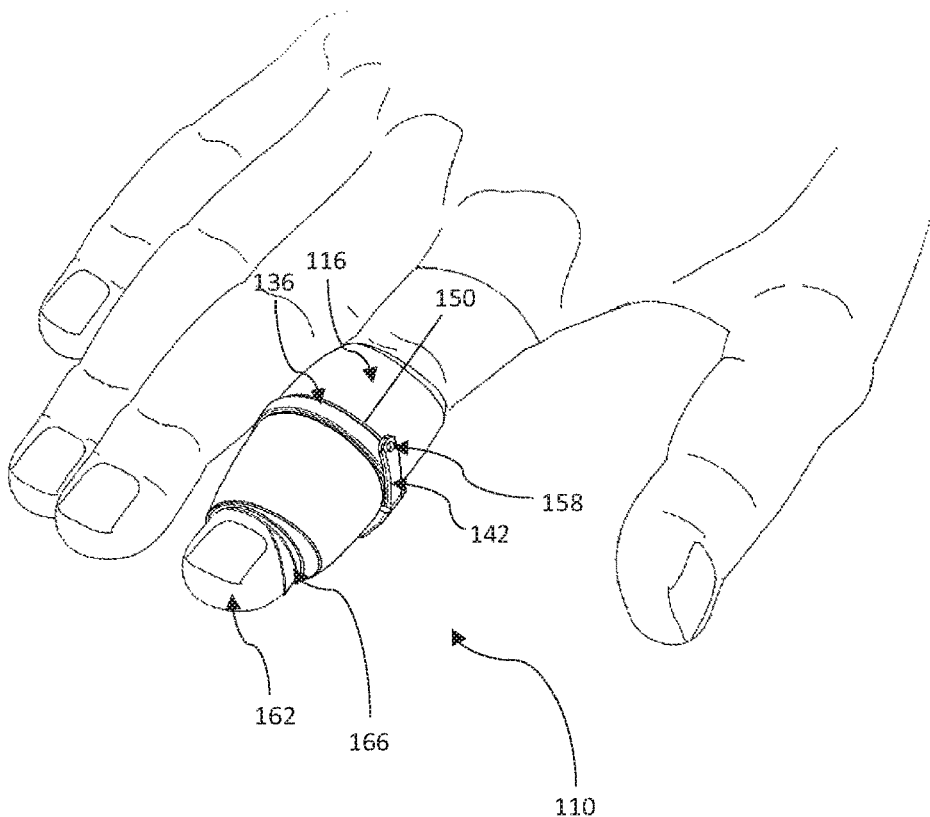

Referring now to FIGS. 7 and 8 which show a second aspect of the invention, there is provided a covering device 110 for covering and protecting a wound (not shown). The covering device 110 includes a substantially shell-shaped cover member 116 for covering the wound (not shown) and a retaining arrangement 118 for retaining the cover member 116 in a wound covering condition wherein the wound is covered and protected.

The shell-shaped cover member 116 has a substantially arcuate profile for allowing a wound in a body part, such as a limb, appendage or digit 162 as shown in the Figures, to be covered and protected in a wound covering condition. In particular, the cover member 116 is sized, shaped and configured to cover a wound located in a joint of a body part and permit substantially unencumbered displacement of the body part in the wound covering condition. Further, the cover member 116 is sized and shaped to accommodate and overlay a dressing or bandage 166 applied to a wound (not shown) in a body part. The cover member 116 has a substantially spheroidal shape, typically resembling a portion of a substantially spherical shell. More particularly, the cover member 116 is in the shape of a quarter spherical or half hemispherical shell.

The cover member 116 is manufactured from an elastic or flexible material for allowing covering of varying contours of a body part and allowing the cover member 116 to at least partially wrap around a body part and overlay itself in the wound covering condition. Although not shown, it is to be appreciated that the flexibility and elasticity of the cover member 116 further allows a user to cover wounds in body parts at varying angles depending on the position of the wound on the body part whilst maintaining substantially uniform application of force or pressure of the cover member to and around the body part and/or a dressing or bandage. In particular, the cover member 116 is manufactured from any suitable flexible synthetics or plastics material or composite of materials which include any one or more of the group including polypropylene, polycarbonate, polyethylene, silicone, nylon, rubber, vulcanised rubber, reinforced vulcanised rubber, butyl rubber and polyvinyl chloride.

The cover member 116 includes a gripping means in the form of a ridge or tooth formation (not shown) for gripping skin surrounding a wound (not shown) in a body part and assisting in retaining the cover member 116 in the wound covering condition. The tooth or ridge formation (not shown) is typically located on an inner surface or underside (not shown) of the cover member 116, for allowing gripping of a wound dressing or bandage 166 applied to a wound (not shown) for assisting in retaining the cover member 116 and the wound dressing or bandage 166 in the wound covering condition. Alternatively, the gripping means is in the form of an adhesive (not shown) for allowing the cover member 116 to adhere to skin surrounding a wound (not shown) so as to seal the wound off and inhibit the ingress of fluid, dirt, bacteria, or any other harmful matter into the wound (not shown). In addition, the adhesive can be configured to adhere to a wound dressing or bandage 166 applied to the wound.

The cover member 116 includes an absorbing member (not shown) for absorbing excess blood or fluid which is typically expelled from a wound.

The retaining arrangement 118 is mounted on the cover member 116. The retaining arrangement 118 includes an elongate member 136 which extends from an end region (not shown) of the cover member 116. The retaining arrangement 118 further includes a receiving zone in the form of an aperture (not shown) for receiving a free end region 142 of the elongate member 136 therein. The aperture (not shown) is sized, shaped and configured to receive the free end region 142 of the elongate member 136 therethrough. The retaining arrangement 118 further includes a retaining formation in the form of a rack-and-ratchet assembly (not shown) for retaining the elongate member 136 in position relative the receiving zone (not shown). The rack-and-ratchet (not shown) assembly typically includes engaging tooth formations extending from the elongate member 136 and a wall (not shown) of the receiving zone (not shown), respectively. Alternatively, the retaining arrangement 118 is in the form of any suitable clamping assembly (not shown) for clamping an overlaying free end region of the elongate member 136 relative itself and the cover member 116 in the wound covering condition. Although not shown, a plurality of receiving zones (not shown) can be defined at various positions in the cover member 116 for accommodating various angular configurations of the cover member 116 relative a body part. The retaining arrangement 118 is manufactured from any suitable flexible synthetics, plastics or metallic material which includes any one or more of the group including polypropylene, polycarbonate, polyethylene, silicone, nylon, rubber, vulcanised rubber and polyvinyl chloride.

A locating formation in the form of an elongate recess 150 is defined in the cover member 116, typically an outer surface 152 thereof, for locating the elongate member 136 relative the cover member 116 when the elongate member 136 overlays the cover member 116, typically during the pipe sealing condition. The elongate recess 150 extends substantially along a length of the cover member 116. The elongate recess 150 is sized and shaped to correspond to the size and shape of the elongate member 136 so as to allow seating thereof in the elongate recess 150 in the wound covering condition. Although not shown, the elongate recess 150 can include tooth formations (not shown) which are sized, shaped and configured to engage with the tooth formations, only shown in FIG. 2 and depicted by reference numeral 46.1, extending from the elongate member 136 for assisting in retaining the cover member 116 in the wound covering condition.

A release mechanism (not shown) is provided for allowing the elongate member 136 to be released from the retaining formation (not shown) and displaced relative the receiving zone (not shown) out of the wound covering condition.

It is to be appreciated that although not shown in FIGS. 5 and 6, the cover member 116, retaining arrangement 118 and locating formation are similar to the cover member 16, retaining arrangement 18 and locating formation as described in the first aspect of the invention.

The cover member 116 and retaining arrangement 118 are integrally formed and manufactured from rubber. Although not shown, in this case, the retaining arrangement 118 can include a pair of rings mounted on the cover member 116 for receiving and retaining a free overlaying end region of the cover member 116 during wrapping thereof around a leak in a pipe. First and second rings of the pair (not shown) are sized, shaped and configured to receive the free end region of the cover member 116 therethrough and allow a user to loop the cover member 116 back over the second ring, back through the first ring and pull the free end region so as to allow the cover member 116 to overlay itself and tighten into the pipe sealing condition.

Figure 9:
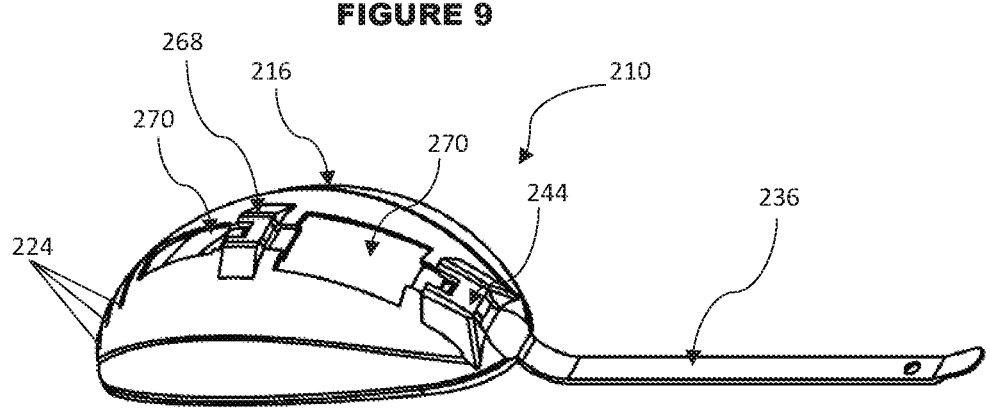
FIGS. 9 to 11 are three-dimensional, side and plan views of a third embodiment of the covering device in accordance with the invention.
Figure 10:
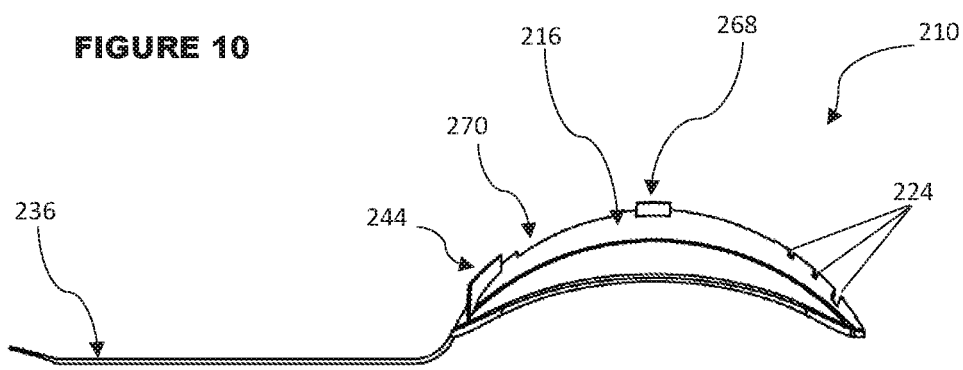
Figure 11:
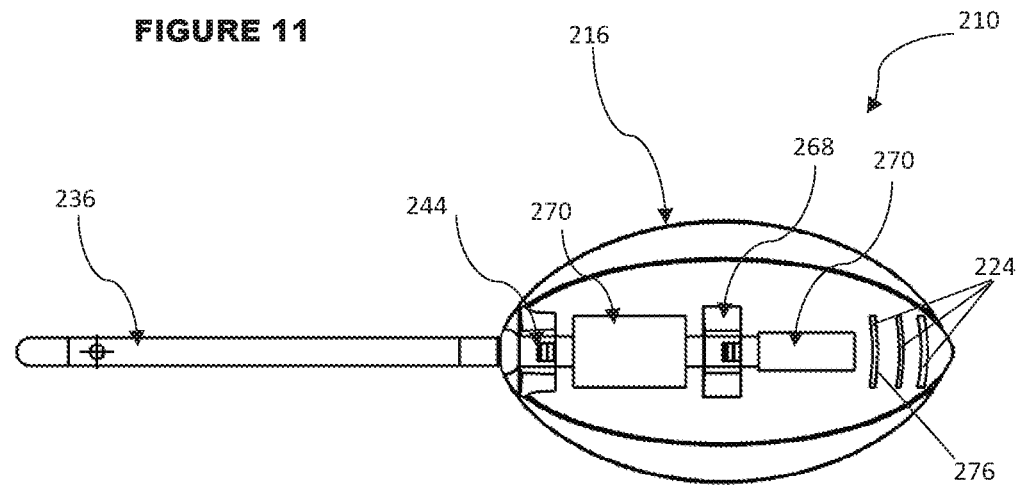

Referring now to FIGS. 9 to 11, reference numeral 210 refers generally to a third embodiment of a covering device in accordance with the invention. In this embodiment, a second retaining arrangement, in the form of a rack-and-ratchet assembly 268, is provided for assisting in retaining an overlaying free end region (not shown) of an elongate member 236 in seated abutment with an overlaid portion of the cover member 216 in a pipe sealing, wound covering or electrical insulating condition.

The second retaining arrangement includes apertures 270 which are defined in the cover member 216 for allowing an overlaying free end region (not shown) of the elongate member 236 to be tucked between layers of overlapping cover member 216 or between the elongate wrapping member (not shown) and the cover member 216.

Figure 12:
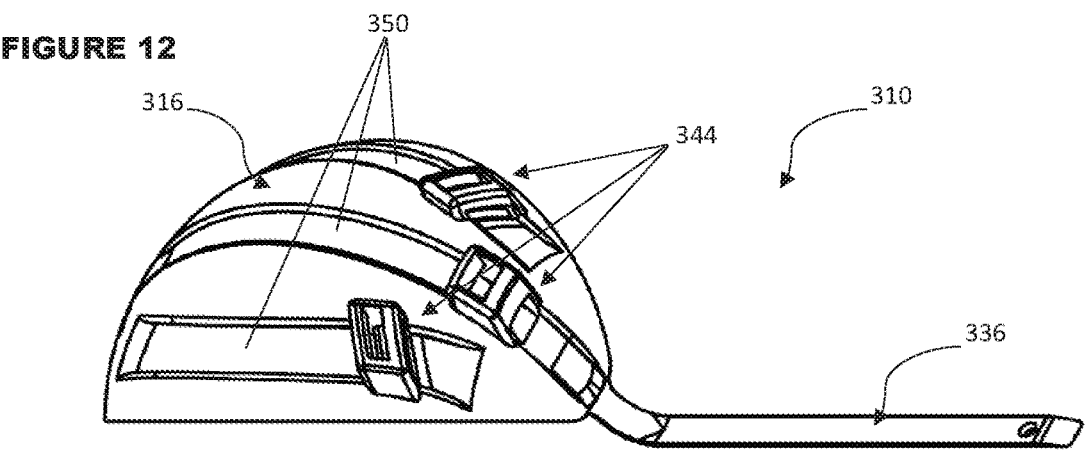
FIGS. 12 to 14 are three-dimensional, side and plan views of a fourth embodiment of the covering device in accordance with the invention.
Figure 13:
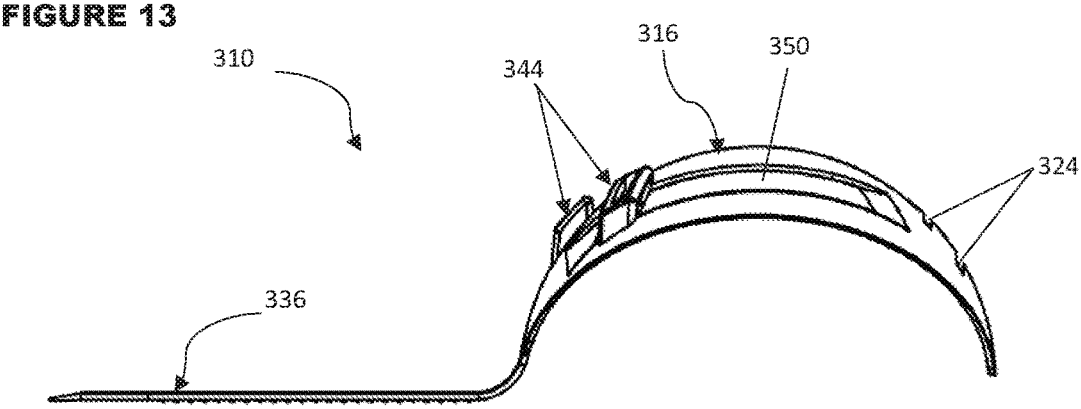
Figure 14:
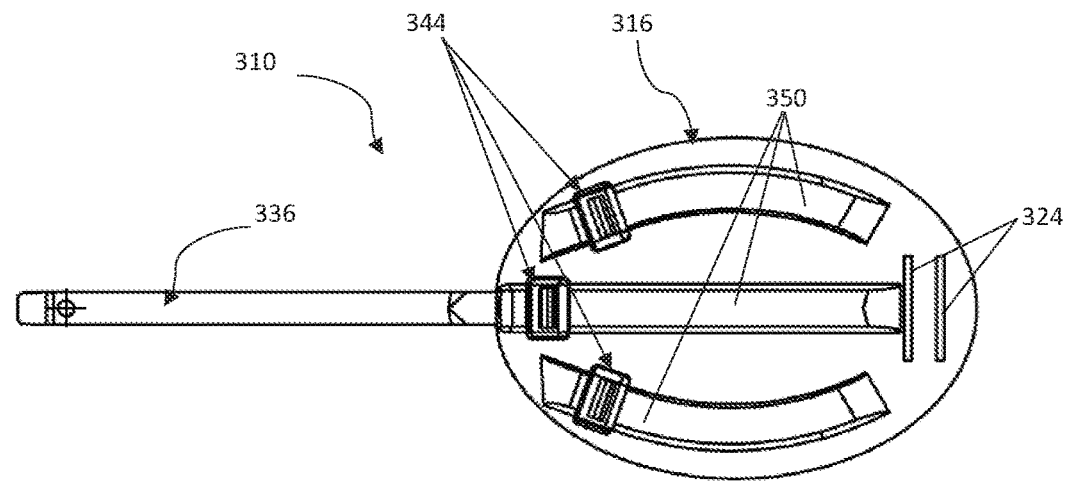
Figure 15:
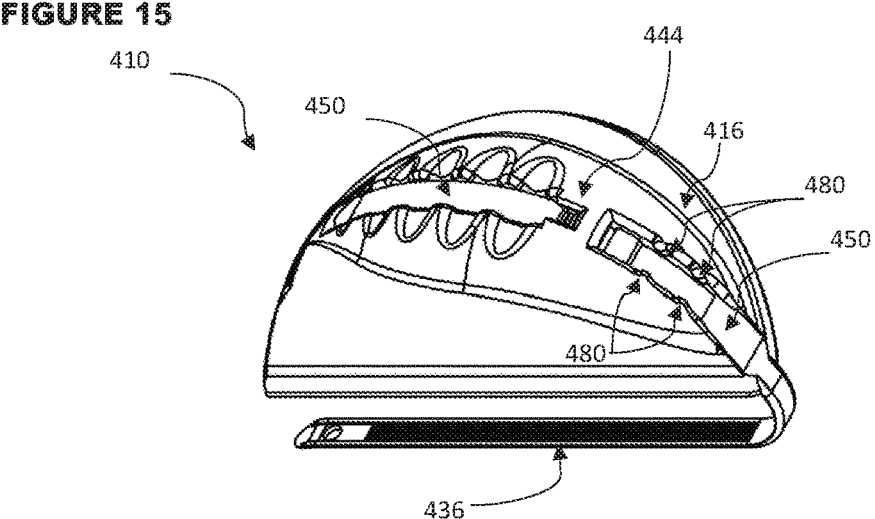
FIGS. 15 to 17 are three-dimensional, side and plan views of a fifth embodiment of the covering device in accordance with the invention.
Figure 16:
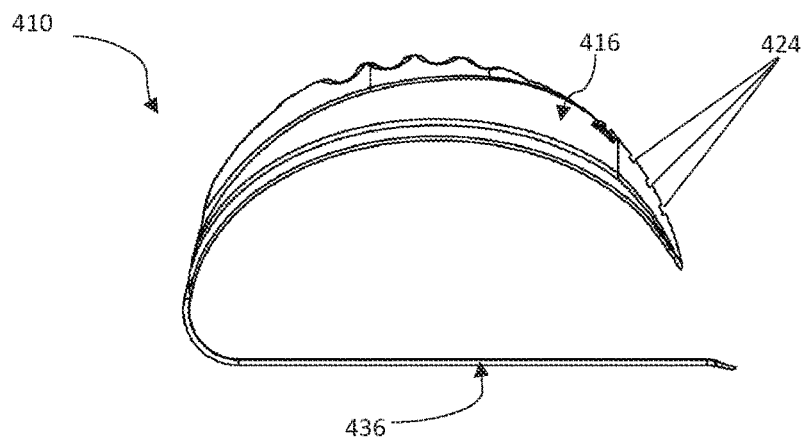
Figure 17:
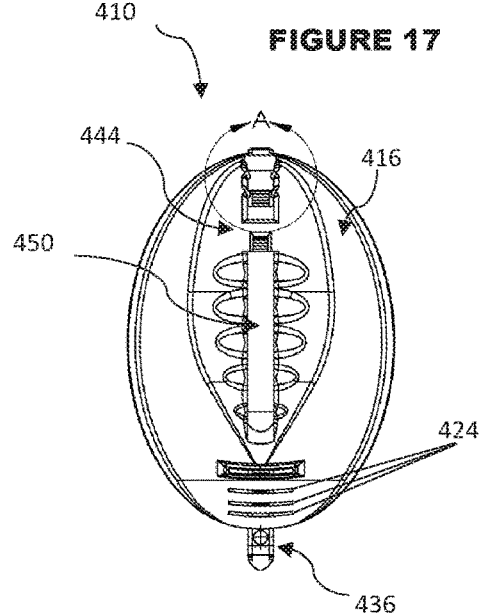
Figure 18:
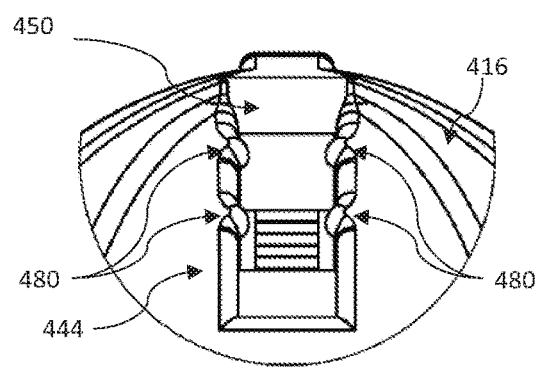
FIG. 18 is an enlarged plan view of the covering device shown in FIGS. 15 to 17.

Referring now to FIGS. 12 to 14, reference numeral 310 refers generally to a fourth embodiment of a covering device in accordance with the invention. In this embodiment, a trio of retaining formations in the form of rack-and-ratchet assemblies 344 are provided on the cover member 316 for retaining an elongate member 336 in position relative a corresponding trio of elongate locating formations 350, typically when the elongate member 336 is wrapped around the cover member 316. The trio of rack-and-ratchet assemblies 344 and corresponding locating formations 350 are spaced apart on the cover member 316 for accommodating possible misalignments between the elongate member 336 and cover member 316 when wrapping the cover member 316 around a pipe, limb, joint or insulative electrical cover.

Referring now to FIGS. 15 to 18, reference numeral 410 refers generally to a fifth embodiment of the covering device in accordance with the invention. In this embodiment, a locating formation in the form of an elongate recess 450 includes narrowed portions 480 for facilitating retention of the elongate member 436 in position relative the cover member 416 in the covering condition.

Figure 19:
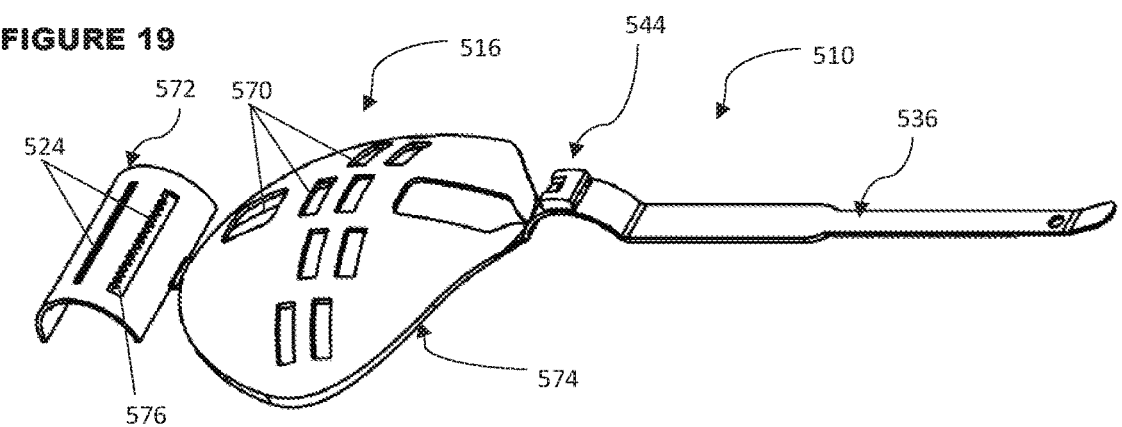
FIGS. 19 to 21 are three-dimensional, side and plan views of a sixth embodiment of the covering device in accordance with the invention.
Figure 20:
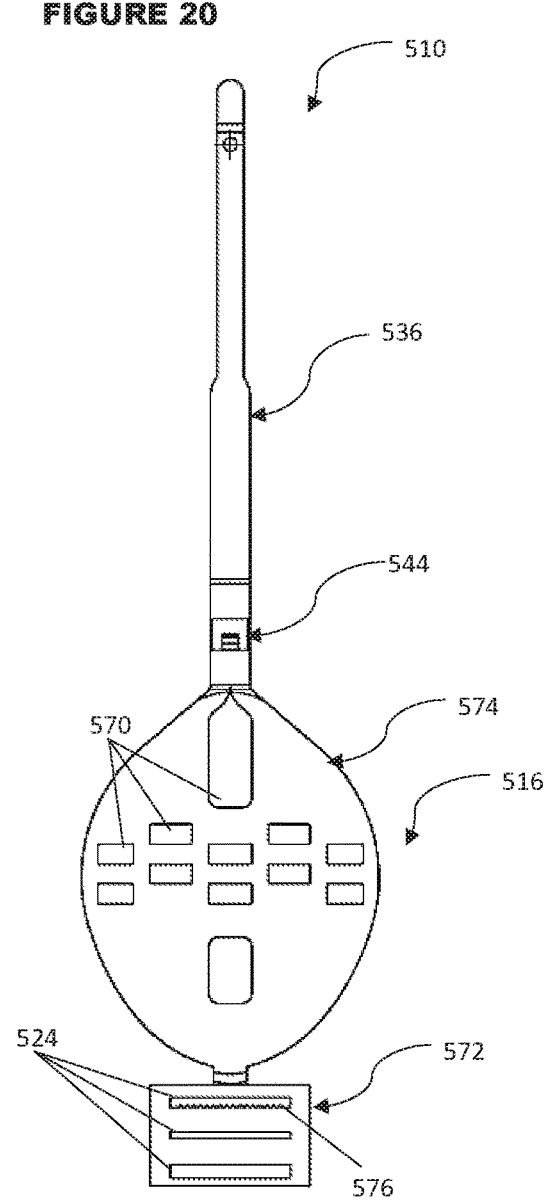
Figure 21:
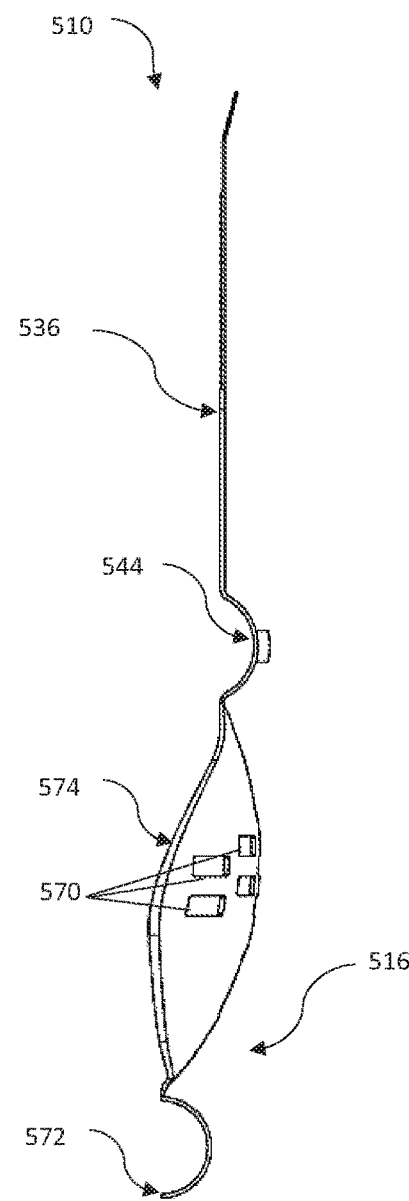

Referring now to FIGS. 19 to 21, reference numeral 510 refers generally to a sixth embodiment of the covering device in accordance with the invention. In this embodiment, the cover member 516 includes a first portion 572 sized, shaped and configured to attach to and overlay an initial part of an elongate wrapping member (not shown), and a second portion 574 sized, shaped and configured to be wrapped around the first portion 572 and completely overlay the wrapping member (not shown) in a wrapped condition.

The first portion 572 of the cover member 516 is substantially cylindrical in shape and includes elongate apertures 524 therein for receiving an end region of the wrapping member 536 and allowing a user to loop the wrapping member 536 over itself in use. The elongate apertures 524 include tooth formations 576 defined at an edge thereof for assisting in retaining the wrapping member (not shown) in position relative the cover member 516 in the wrapped condition.

The second portion 574 of the cover member 516 is shell-shaped so as to conform to the shape of the wrapping member (not shown) in the wrapped condition and to the curvature of a pipe, limb, digit or insulative electrical cover around which the cover member 516 is being wrapped. The second portion 574 includes a plurality of apertures 570 defined therethrough for receiving an overlaying free end region of an elongate member 536 therein after wrapping thereof around the cover member 516 and allowing tucking of the overlaying free end region of the elongate member 536 between layers of overlapping cover member 516 or between the elongate wrapping member (not shown) and the cover member 516. The plurality of apertures 570 are spaced apart from each other and positioned in various locations on the second portion of the cover member for accommodating misalignments between the cover member 516 and the elongate member 536 during wrapping thereof around a pipe, limb, digit or insulative electrical cover in use, typically so as to ensure a tight fit of the cover member 516 therearound.

Figure 22:
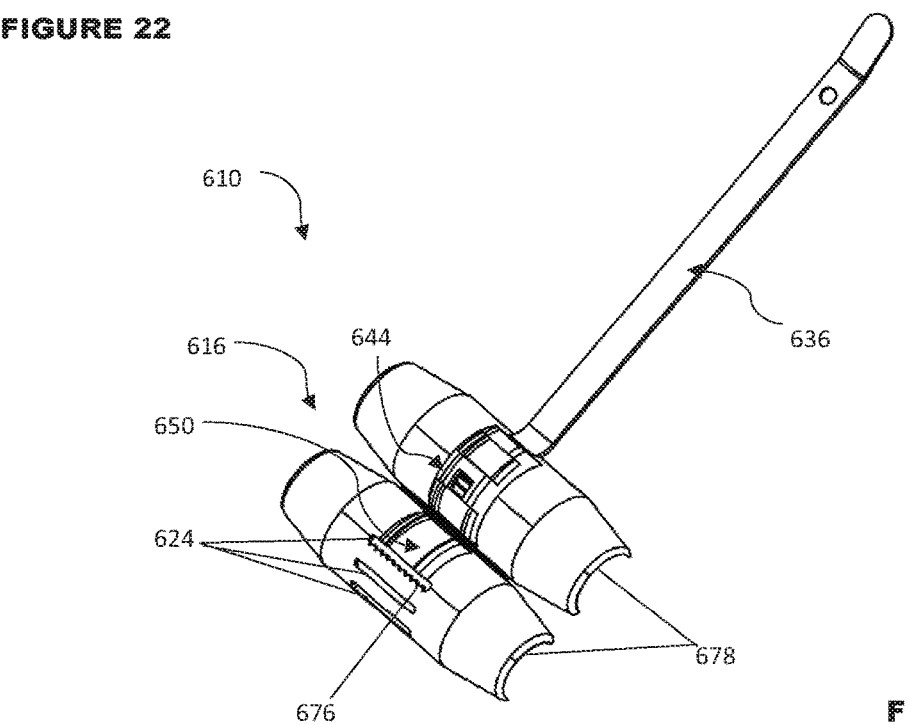
FIGS. 22 to 24 are three-dimensional, side and plan views of a seventh embodiment of the covering device in accordance with the invention.
Figure 23:
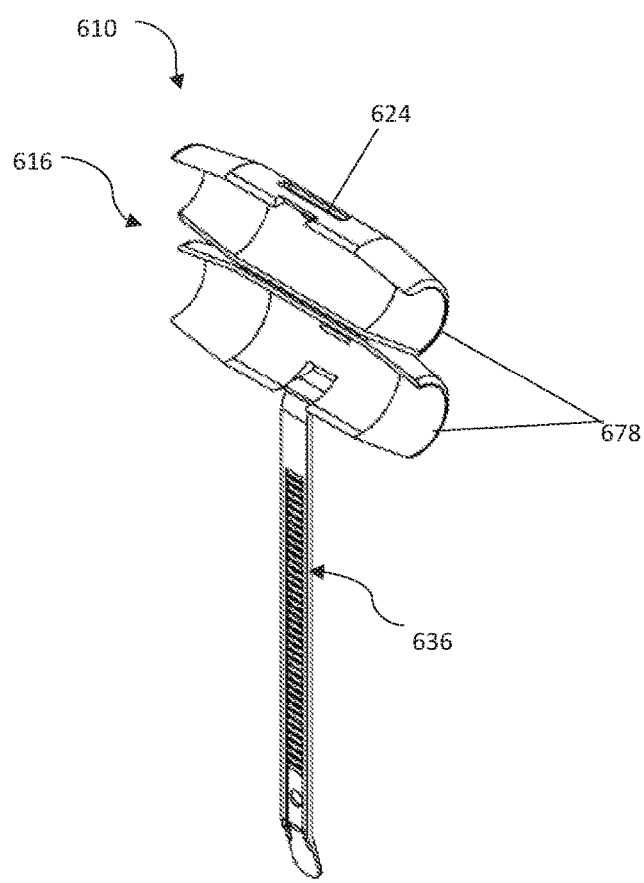
Figure 24:
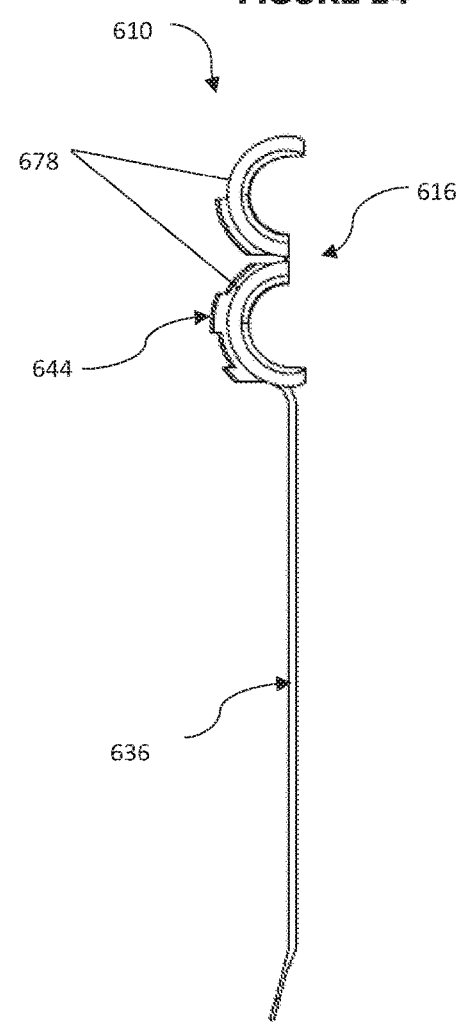

Referring now to FIGS. 22 to 24, reference numeral 610 refers generally to a seventh embodiment of the covering device in accordance with the invention. In this embodiment, the covering device 610 includes a cover member 616 which comprises a pair of substantially arcuate segments 678 which are pivotally connected to each other. The segments 678 are substantially curved in a first, longitudinal, direction to accommodate the general curvature of a pipe, limb, digit or insulative electrical cover and in a second, transverse, direction to accommodate a curved profile of a wrapping member (not shown) in a wrapped condition relative the pipe, limb, digit or insulative electrical cover.

Figure 25:
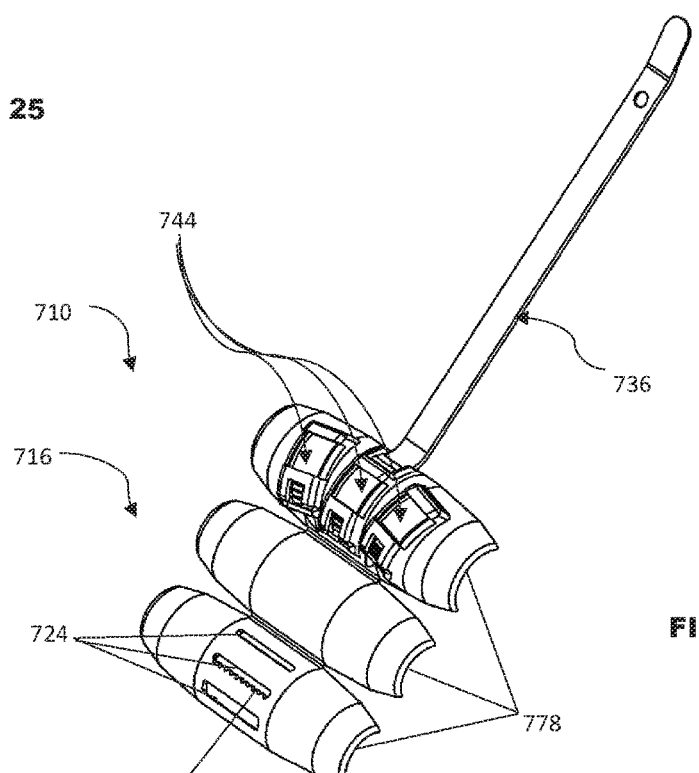
FIGS. 25 to 27 are three-dimensional, side and plan views of an eighth embodiment of the covering device in accordance with the invention.
Figure 26:
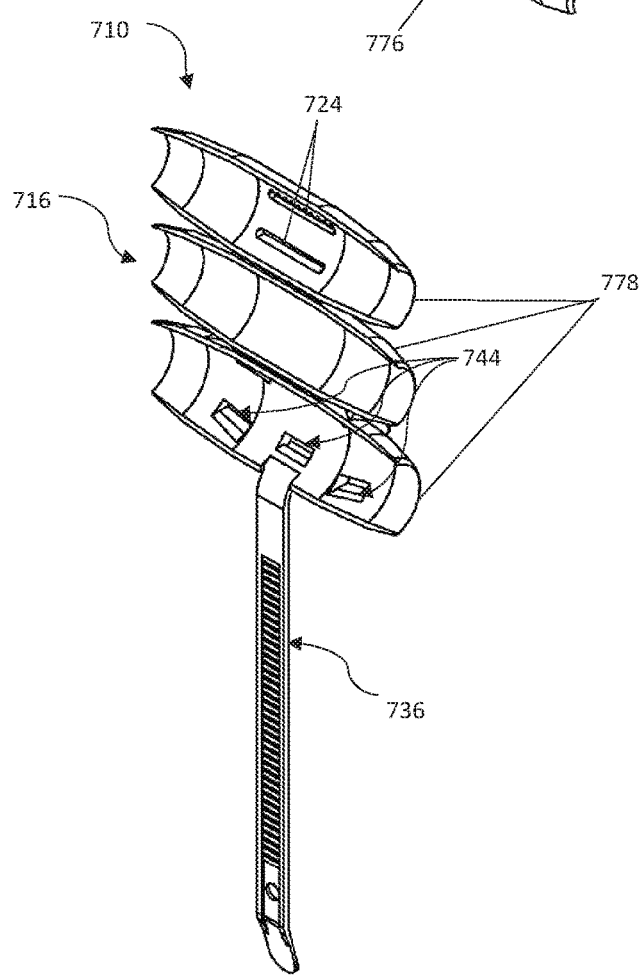
Figure 27:
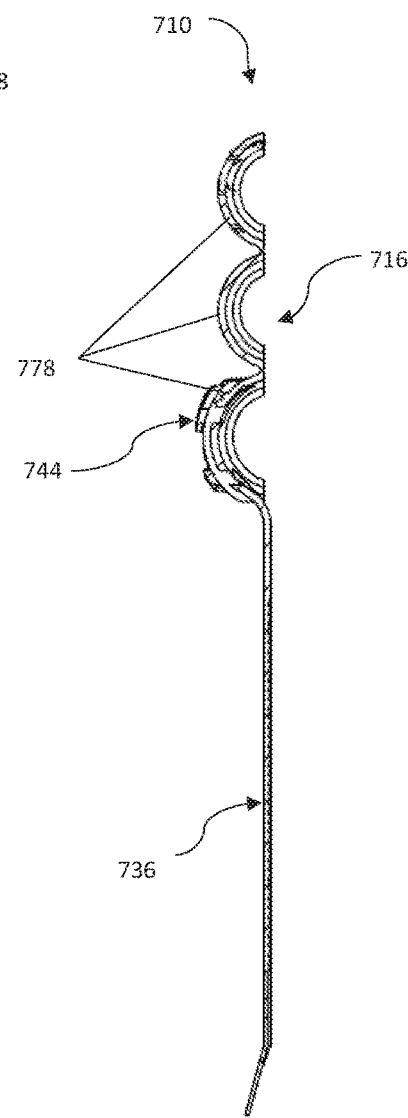

Referring now to FIGS. 25 to 27, reference numeral 710 refers generally to an eighth embodiment of the covering device in accordance with the invention. In this embodiment, the covering device 710 includes a cover member 716 which comprises a trio of substantially arcuate segments 778 which are pivotally connected to each other. The segments 778 are substantially curved in a first, longitudinal, direction to accommodate the general curvature of a pipe, limb, digit or insulative electrical cover and in a second, transverse, direction to accommodate a curved profile of a wrapping member (not shown) in a wrapped condition relative the pipe, limb, digit or insulative electrical cover.

Further, a trio of retaining formations in the form of rack-and-ratchet assemblies 768 are provided for accommodating possible misalignments between the elongate member 736 and cover member 716 when wrapping the cover member 716 around a pipe, limb, joint or insulative electrical cover.

It is to be appreciated that, although not shown in the Figures, the covering devices 10, 110, 210, 310, 410, 510, 610 and 710 can be sized, shaped and configured to be wrapped around an outer, e.g., insulative, covering of electrical wiring so as to facilitate substantial sealing of any crack, slit or opening therein so as to inhibit the ingress of fluid such as water therein.

It is to be appreciated that, although not shown in the Figures, the sealing devices 10, 110, 210, 310, 410, 510, 610 and 710 can be sized, shaped and configured to be wrapped around an exhaust pipe so as to facilitate substantial sealing of any crack, slit or opening therein so as to inhibit the egress of exhaust gases therefrom.

Although only certain embodiments of the invention have been described herein, it will be understood by any person skilled in the art that other modifications, variations, and possibilities of the invention are possible. Such modifications, variations and possibilities are therefore to be considered as falling within the spirit and scope of the invention and hence form part of the invention as herein described and/or exemplified. It is further to be understood that the examples are provided for illustrating the invention further and to assist a person skilled in the art with understanding the invention and is not meant to be construed as unduly limiting the reasonable scope of the invention.

At least some embodiments of the present disclosure may provide a simple and/or cost-effective solution for sealing a leak in a pipe with an elastic material without the need to use additional parts, such as cable ties, to assist in sealing the leak in the pipe. Further, embodiments may provide an elastic pipe wrapping member which is configured to form to the shape of the pipe, particularly of the repair area of the pipe, thereby ensuring that the leak is covered and sealed. Further, embodiments may include a shell-shaped cover member, particularly a half hemispherical shell-shaped cover member, which is especially suited for and capable of tightly and snugly covering pipe wrapping members wrapped around leaks in straight and bent pipes as well as in joints between pipes and pipes of varying diameter. The shape further facilitates conditions where the cover member covers a pipe wrapping member at an angle relative a longitudinal axis of pipe. Further, the cover member and retaining arrangement may be suitable for covering and protecting a wound or for retaining a wound dressing or bandage in position when wrapped around a wound in a joint in a limb, appendage or digit, while permitting substantially unencumbered displacement of the limb, appendage or digit during a wound covering condition or during injured limb immobilisation. The shape and flexibility of the cover member may beneficially be capable of applying substantially equal pressure along a width thereof when tightened, typically as a result of a generally central portion of the cover member deforming towards a covered object during tightening. Yet further, the cover member is capable of deforming towards a side thereof to form a substantially conical shape for sealing leaks in pipes of varying size and leaks in joints between different sized pipes. Embodiments of the disclosure may also be capable of sealing pipes having bends of more the 90 degrees. Even further, the embodiments of the present disclosure may provide a cover member that can be tightened around the wrapping member by hand, e.g., without requiring the assistance of tools.

What is claimed is:

1. A covering device, comprising:
   an elongate wrapping member configured to be wrapped around and overlay an opening in an object in a wrapped condition;
   a substantially shell-shaped cover member for covering the wrapping member substantially in the wrapped condition, wherein the shell-shaped cover member is curved in both longitudinal and transverse directions; and
   a retaining arrangement for retaining the cover member and the wrapping member in position relative the object in a covering condition.

2. A covering device as claimed in claim 1 further comprising a connecting arrangement for allowing releasable interconnection between the wrapping member and the cover member, the connecting arrangement including a receiving formation for receiving the wrapping member therein, the receiving formation being sized, shaped and configured to receive and retain the wrapping member in a connected condition relative the cover member.

3. A covering device as claimed in claim 2 wherein the receiving formation is sized, shaped and configured to allow relative displacement between the cover member and the wrapping member in the wrapped condition so as to facilitate substantial overlaying of the wrapping member by the cover member, the receiving formation being in the form of a plurality of slots which are defined in the cover member for receiving the wrapping member therethrough for allowing a plurality of loops to be formed allowing the wrapping member to substantially overlay and retain itself in the connected condition.

4. A covering device as claimed in claim 1 wherein the shell-shaped cover member has a substantially arcuate profile so as to correspond with the curvature of the object having an opening to be covered and the curvature of the wrapping member in the wrapped condition.

5. A covering device as claimed in in claim 1 wherein the cover member has a substantially spheroidal shape.

6. A covering device as claimed in in claim 1 wherein the cover member is in the shape of any one of a quarter spherical shell, half hemispherical shell, or a spheroidal cap.

7. A covering device as claimed in in claim 1 wherein the cover member is sized so as to allow the cover member to overlay the wrapping member in the wrapped condition, the cover member having a width that allows a free end region of the cover member to overlay itself at least partially in the covering condition.

8. A covering device as claimed in in claim 1 wherein the cover member includes a gripping formation comprising a plurality of ridges for gripping the elongate wrapping member in the covering condition, the plurality of ridges extending inwardly the cover member to grip the wrapping member in the covering condition.

9. A covering device as claimed in claim 8 wherein the ridges extend at an angle away from the cover member for allowing directional gripping of the wrapping member thereby permitting tightening of the cover member around the wrapping member whilst inhibiting loosening of the cover member in the covering condition.

10. A covering device as claimed in claim 8 wherein ridges extend from an outer surface of the cover member, which ridges are configured to engage complementally the inwardly extending ridges for assisting in retaining the cover member in the covering condition.

11. A covering device as claimed in in claim 1 wherein the cover member is manufactured from one or more materials that permit tightening and flush overlaying thereof with the wrapping member into the covering condition, the one of the materials being selected from the group consisting of polypropylene, polycarbonate, polyethylene, silicone, nylon, rubber, vulcanised rubber, reinforced vulcanised rubber, butyl rubber and polyvinyl chloride.

12. A covering device as claimed in claim 1 wherein the retaining arrangement is mounted on the cover member, the retaining arrangement including an elongate member which extends from the cover member from an end region thereof opposite the connecting arrangement, the retaining arrangement further including a receiving zone for receiving a free end region of the elongate member therein, the receiving zone being in the form of a slot which is sized, shaped and configured to receive the free end region of the elongate member therethrough.

13. A covering device as claimed in claim 12 wherein a plurality of receiving zones are defined at various positions in the cover member for accommodating various angular configurations of the cover member relative a wrapped object.

14. A covering device as claimed in claim 12 wherein retaining arrangement includes a retaining formation comprising a rack-and-ratchet assembly for retaining the elongate member in position relative the receiving zone, the rack and ratchet assembly including engaging tooth formations extending from the elongate member and a wall of the receiving zone, respectively.

15. A covering device as claimed in claim 12 wherein a locating formation in the form of an elongate recess is defined in the cover member on an outer surface thereof, for locating the elongate member relative the cover member when the elongate member overlays the cover member during the covering condition.

16. A covering device as claimed in in claim 12 wherein a second retaining arrangement is provided for assisting in retaining an overlaying free end region of the elongate member in abutment with an overlaid portion of the cover member in the covering condition, the second retaining arrangement being in the form of any one of the group including a band-like member for receiving and retaining the overlaying free end region of the elongate member in seated abutment with the cover member, a rack-and-ratchet assembly, an aperture defined in the cover member for allowing the overlaying free end region of the elongate member to be tucked between layers of overlapping cover member, and an aperture defined in the cover member for allowing the overlaying free end region of the elongate member to be tucked between the cover member and the wrapping member.

17. A covering member as claimed in claim 1 wherein the covering member is configured for use in covering and sealing a leak in a pipe.

18. A covering member as claimed in claim 1 wherein the covering member is configured for use in covering and protecting a wound in a body part.

19. A covering device for covering and sealing a leak in a pipe, the covering device comprising:
- an elongate pipe wrapping member configured to be wrapped around and overlay a leak in a pipe in a wrapped condition;
- a substantially shell-shaped cover member for covering the pipe wrapping member substantially in the wrapped condition, wherein the shell-shaped cover member is curved in both longitudinal and transverse directions; and
- a retaining arrangement for retaining the cover member and the pipe wrapping member in position relative the pipe in a pipe sealing condition.

* * * * *